United States Patent
Dorn et al.

(10) Patent No.: US 8,407,719 B2
(45) Date of Patent: Mar. 26, 2013

(54) PROGRAM CODE COMPRISING A NUMBER OF PROGRAM CODE PACKAGE GROUPS STORED ON STORAGE UNITS

(75) Inventors: Karlheinz Dorn, Kalchreuth (DE); Vladyslav Ukis, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 522 days.

(21) Appl. No.: 12/641,354

(22) Filed: Dec. 18, 2009

(65) Prior Publication Data

US 2010/0175071 A1 Jul. 8, 2010

(30) Foreign Application Priority Data

Jan. 7, 2009 (DE) .......................... 10 2009 004 002

(51) Int. Cl.
*G06F 3/00* (2006.01)
*G06F 9/44* (2006.01)
*G06F 9/455* (2006.01)
(52) U.S. Cl. .................... 719/313; 717/177; 717/120
(58) Field of Classification Search .................. None
See application file for complete search history.

(56) References Cited

U.S. PATENT DOCUMENTS

| | | | |
|---|---|---|---|
| 6,275,871 B1 | 8/2001 | Reinfelder | |
| 2005/0144615 A1* | 6/2005 | Chen et al. | 717/169 |
| 2006/0041450 A1* | 2/2006 | Dugan | 705/2 |
| 2006/0112387 A1* | 5/2006 | Butt et al. | 717/177 |
| 2009/0013309 A1* | 1/2009 | Shavlik | 717/120 |

OTHER PUBLICATIONS

Composing Distributed Objects in CORBA; Jeff Magee et al.: "Composing Distributed Objects in CORBA", Autonomous Decentralized Systems, 1997, Proc. ISADS 97; 3. Int. Symp., p. 257-263, Apr. 9-11, 1997, DOI: 10.1109/ISADS.1997.590629; 1997; Apr. 9, 1997.
CORBA: Integrating Diverse Applications Within Distributed Heterogeneous Environments; St. Vinoski: "CORBA: Integrating Diverse Applications Within Distributed Heterogeneous Environments", Communications Magazine, IEEE, vol. 35, No. 2, p. 46-55, Feb. 1997, DOI: 10.1109/35.565655; 1997; Feb. 1, 1997.
DE Office Action mailed Dec. 4, 2012.

* cited by examiner

*Primary Examiner* — Kenneth Tang
(74) *Attorney, Agent, or Firm* — Harness, Dickey & Pierce, P.L.C.

(57) ABSTRACT

A software platform is provided for a hospital for example, wherein software modules (program code packages) are assigned in groups to different levels. In at least one embodiment, the presence of software interfaces allows software modules of different levels to be stored and run on different computer units with a data processing facility and storage unit, thus allowing communication between different levels by way of a data line. In at least one embodiment, this allows tasks to be moved out of the hospital, thereby saving costs.

21 Claims, 2 Drawing Sheets

| | Concept 1 | Concept 2 | Concept 3 | Concept 4 |
|---|---|---|---|---|
| First group | | On client | On client | On client |
| Second group | On client | On client | On server | On server 1 |
| Third group | | On server | | On server 2 |

FIG 2

|  | Concept 1 | Concept 2 | Concept 3 | Concept 4 |
|---|---|---|---|---|
| First group | On client | On client | On client | On client |
| Second group | | | On server | On server 1 |
| Third group | | On server | | On server 2 |

PROGRAM CODE COMPRISING A NUMBER OF PROGRAM CODE PACKAGE GROUPS STORED ON STORAGE UNITS

PRIORITY STATEMENT

The present application hereby claims priority under 35 U.S.C. §119 on German patent application number DE 10 2009 004 002.1 filed Jan. 7, 2009, the entire contents of which are hereby incorporated herein by reference.

FIELD

At least one embodiment of the invention generally relates to a so-called software platform. In at least one embodiment, this is intended to be suitable for use in a hospital.

BACKGROUND

A software platform comprises a totality of program code, which is characterized in that the program code is made up of program code packages. The program code packages are simply software modules. Each program code package can run individually on a data processing facility. While running on a data processing facility a program code package causes steps to be performed in a sequence. The program code packages in a software platform can be combined into groups. There is a hierarchical group order here: software modules from a group high up in the hierarchical order can call up software modules from the next level down so that these can run. In other words in a step performed on the basis of a program code package of a predetermined level of the hierarchy steps, the performance of steps is brought about by running a program code package of the level of the hierarchy following the predetermined level.

In addition to the above-mentioned software modules in the hierarchy, the platform also includes specifications according to which applications have to be structured, in order to be able to run on the platform and to be able to make use of the above-mentioned software modules in the process. The software platform also includes the so-called runtime architecture, in other words elements, which ensure that the applications and modules can be instanced, administered (according to so-called life-cycle management), linked and run.

Software solutions for hospitals are characterized in that all the software that may be required in any manner, in other words all the software modules of a software platform, are stored on storage units in the hospital. The storage units are assigned data processing facilities. In standard hospital routine the treating physicians constantly use one computer program or another. So the software is the subject of extreme outlay. The software must first be bought, then installed, then constantly maintained and tailored to ambient conditions. Since software is a product with a short life, it has to be replaced at short time intervals by updated software, generally a new version of the previous program. A computer expert has to be present for all these procedures. The ubiquity of software in modern hospitals means that such hospitals have a considerable amount of work to do in addition to actual medical and care-providing activities. This work is also associated with a high level of cost.

SUMMARY

The inventors have found that it could be desirable if hospitals were able to outsource tasks resulting from the use of software. This should reduce costs as well.

At least one embodiment of the invention provides a specific software platform, which is suitable for use by hospitals.

In at least one embodiment of the invention, software modules from two consecutive groups in the hierarchical order can exchange data with one another by way of a data line. To this end corresponding interfaces are provided by software means. Expressed by the term "program code package" this means that program code packages from two predetermined groups, which follow one another in the hierarchical order, have program code package parts (namely to provide a software interface), which bring about the performance of respective steps such that in a step performed on the basis of a program code package of the first predetermined group, at least one data item is sent, which is received in a step performed on the basis of a program code package of the second predetermined group. The program code package parts should be designed so that the at least one data item can be sent from a first data processing facility at a first location to a data processing facility at a second location by way of a data line.

It should be noted that the provision of such program code package parts is not a standard measure. The program code package wishing to send a data item runs on the first data processing facility and the program code package wishing to receive a data item runs on the second data processing facility. Steps have to be taken first to link the two data processing facilities to one another. In software language this means that a data channel has to be produced, by way of which the at least one data item can be sent. This has already proven to be non-standard in the past but a method for providing such software interfaces is the subject matter of U.S. Pat. No. 6,275,871 B1, the entire contents of which are hereby incorporated herein by reference. The very method described there can be deployed in the present instance, in other words program code package parts of two consecutive groups in the hierarchical order can be equipped correspondingly.

The fact that software modules can exchange data by way of a data line in the same software platform means that the software modules of the software platform, in other words the program code packages, can be distributed to different computer units, such computer units having a storage unit and a data processing facility (e.g. a microprocessor). Hierarchies of tasks to be executed in operating instructions in a hospital can then be created and program code packages can be assigned to the tasks. Then only the program code packages of the top level of the hierarchy have to be stored in the hospital; all the other program code packages can be stored on a storage unit outside the hospital and can be made to run by an associated data processing facility.

A particularly high level of flexibility is achieved in the distribution of the program code packages, if mutually associated interfaces of the type described above are present for as many as possible and even preferably all group pairs of groups, which follow one another in the hierarchical order, so that the program code packages from both groups have program code package parts, which allow the transmission of data by way of a data line between two data processing facilities. It should be noted that the program code package parts for each group pair can be embodied differently, in particular can be tailored optimally to the tasks of the respective program code packages.

As mentioned above, different groups consisting of at least one program code package can be stored on different storage units with a respectively assigned data processing facility. In particular all groups can be stored respectively on a different storage unit. It is even possible for different program code packages from at least one group to be stored on different storage units with a respectively assigned data processing facility. As mentioned above, at least one storage unit with a respectively assigned data processing facility can be disposed in a hospital, while another storage unit with an associated data processing facility is disposed outside a hospital. The locating of program code packages outside the hospital has the advantage that hospital personnel are not responsible for the installation, maintenance and replacement of the software. The program code packages on storage units outside a hospital can also be used in a multiple fashion, e.g. by a plurality of hospitals. This represents a cost saving: the software only has to be installed, maintained and/or replaced once, not separately for each hospital. There may also be a group discount for software licensing. It should be noted that the inventive provided program code allows such location of program code packages outside the hospital but this is not mandatory: a hospital can always also decide to store all the groups from at least one program code package on a storage unit with an assigned data processing facility. This can be a single storage unit, with the groups preferably being distributed to different storage units with an assigned data processing facility in the hospital. This is also advantageous for the hospital: for example a central server can thus be provided in the hospital, being disposed at a site where its installation is less obtrusive. In contrast other software modules can be located where they are directly required, in particular in the associated departments.

A software platform for a hospital preferably has certain characteristics, which relate to the classification of the groups in the hierarchical order. Thus the group with at least one program code package at the top of the hierarchical order should comprise at least one program code package, which when run brings about the performance of at least one step as a function of a user input (made by way of a user interface). This is expedient because a program code package has to be responsible for processing user inputs and if it is part of the group at the top of the hierarchical order, the program code packages from this group can be located at the location where the user input takes place. In principle all the program code packages from hierarchically lower groups could then be set up at a different location.

This does not mean that the user input cannot bring about the running of programs by way of program code packages of lower order groups indirectly by way of a program code package from the hierarchically top group. It can even prove advantageous for the distribution of tasks to grade the tasks to be performed based on user inputs hierarchically. Such advantages can then be utilized, when the second highest group in the hierarchical order comprises a program code package which, on performance of a predetermined step brought about by the running of a program code package from the highest group in the hierarchical order as a function of a user input also brings about the performance of at least one step as a function of this user input. In other words the program associated with the program code package from the highest group also calls up a lower-order program in at least one step.

The inventively provided software platform, in at least one embodiment, in particular also allows certain programs to be called up from a plurality of higher level programs. A software module at a low level of the hierarchical order therefore does not have to be assigned to just one software module from a higher level but such a software module can be used a number of times. This means that the corresponding program code only has to be made available once, so that storage space is saved and organizational outlay is also reduced. In the words of the claim, a group with at least one program code package that is of a lower order in the hierarchical order than another group should comprise such a program code package, which, when at least two different program code packages from the other (higher) group are respectively run, is respectively prompted in a step in turn to bring about the performance of a step when running.

At least one embodiment of the invention also relates to a storage medium with a program code of the inventively provided characteristics. The storage medium can be a data carrier, which serves to transfer the program code to one or more storage units. The storage medium can itself also comprise such a storage unit. As set out above, the program code allows program code packages to be run on different data processing units and data still to be exchanged. This means that the storage medium comprises at least two storage units, associated respectively with a specific computer unit with a data processing unit. Such a computation unit is then preferably disposed in the hospital and the other is not.

At least one embodiment of the inventive method for processing data based on operating instructions by way of a user interface disposed in a hospital is such that in an chain of data processing facilities consisting of at least two elements an operating instruction causes a step performed by a data processing facility in the chain respectively to bring about the performance of at least one step by a subsequent data processing facility in the chain. The chain thus involves one program calling up another program and the programs running respectively on different data processing facilities. According to at least one embodiment of the invention one data processing facility from the chain, which executes a step brought about by the operating instruction, is disposed outside the hospital. In other words an operating instruction input by way of a user interface disposed in the hospital causes a data processing facility outside the hospital to be activated.

This data processing facility disposed outside the hospital is preferably at least a third element in the chain. The second element in the chain here can optionally be disposed inside the hospital or also outside the hospital. The first instance is particularly advantageous: the user interface can be provided in a hospital department, to which a first data processing facility can be directly assigned. A second data processing facility in the chain is then present at a central location in the hospital, performing other steps based on the operating instruction. This second data processing facility then calls up the third data processing facility outside the hospital.

BRIEF DESCRIPTION OF THE DRAWINGS

An example embodiment of the invention is described below with reference to the drawings, in which FIG. 1 shows a schematic diagram of the structure of an embodiment of an inventively provided software platform and FIG. 2 is a table showing the distribution of software modules of the software platform from FIG. 1 for different arrangement concepts.

DETAILED DESCRIPTION OF THE EXAMPLE EMBODIMENTS

Figure 1:
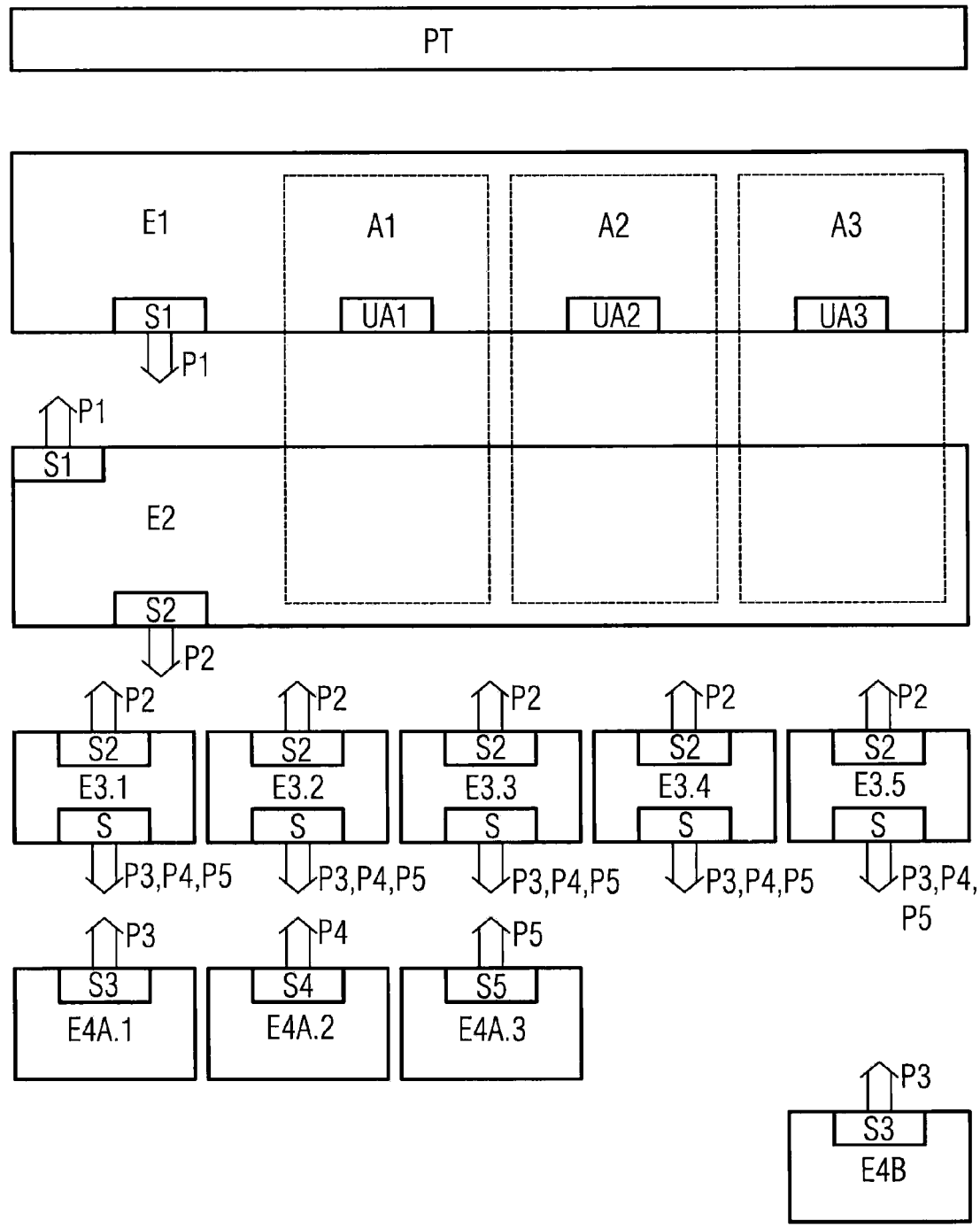

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

An embodiment of the invention provides a software platform for use in a hospital. The software platform is intended to allow the performance of hospital-specific applications of diverse types.

The software platform is to be embodied so that it is possible to elect to move software functions out from the region of the hospital.

In the present instance software modules (i.e. program code packages) are provided for the software platform, these being arranged hierarchically. FIG. 1 shows individual levels of the hierarchical order marked "E" and numbered according to the hierarchical order. The higher the level in the hierarchical order, the more specifically the tasks of the software are designed for the hospital and also for individual hospital departments. In contrast the lower levels are assigned tasks which are requirements for some applications and in particular have of necessity to be performed for a plurality of applications.

On the part of the hospital the software is called up by way of a portal PT. At the highest level E1 is in particular the software responsible for tasks which are responsible for tasks associated with the operation of a system by an operator by way of a user interface. Such tasks in particular consist of generally allowing the operator first of all to make a user input, e.g. by providing specific masks. Also messages are to be fed back to the operator, e.g. specific displays are presented on the screen.

These purely formal tasks are supplemented in typical applications by somewhat more extensive tasks, which are performed by the second level E2. In particular there are applications A1 and A2, and A3, which can be called up by an operator, and during the running of which both software from level E1 and software from level E2 is deployed. It is the case for the software platform as a whole that program code packages from lower levels can be called up respectively at the next level up. Thus the applications A1, A2 and A3 have sub-applications UA1, UA2 and UA3, which are used to call up software from the second level E2.

In the present instance it should also be possible to call up software from a lower level even if said software is not stored on the same storage unit as the calling software and does not run on the same data processing facility as it. This is allowed in that the software modules are provided with respectively appropriate interfaces. These interfaces are marked "S" in FIG. 1 and numbered with reference to specific protocols. A software interface S1 in the software module E1 allows it to communicate with an associated software interface S1 in the software module E2 using a protocol P1. In the present instance an interface can be used for example, which is based on the principles described in U.S. Pat. No. 6,275,871 B1. According to these principles high-order software modules in a hierarchy can transmit data, e.g. a call command by one of the sub-applications UA1, UA2, UA3, by way of data lines between two different data processing facilities.

In a hospital environment application A1 can take the form for example of a functionality for viewing patient images, also referred to as a viewer. The part of the application A1, which is associated with the level E1, then relates to the specific control of the screen while the content of the display is transferred by a program code package from level E2.

In a hospital environment application A2 can take the form of an application allowing image selection as a supplement to the image-displaying application. Application A2 allows a search through computers containing image files, etc. and has the function of a browser.

Finally in a hospital environment application A3 can take the form of a further application, which allows the administration of patient data. It has to be possible to access such patient data constantly throughout the hospital. To this end the patient data must be input and stored in an appropriate format.

From the software module level E2 it is now possible to provide software modules from a lower level, these being referred to in this instance as E3.1, E3.2, E3.3, E3.4 and E3.5. In this instance it should also be possible to separate level E2 and level E3, so that the respective software modules are stored on different storage units and run on different data processing facilities. To this end software interfaces S2 are provided here too, in this instance allowing communication by way of a protocol P2. Conventional types of interface can be used here and known web service protocols can be used as the protocol P2.

In a hospital environment the software module E3.1 can for example take on the task of transferring images from and to the applications, primarily A1 and A2. Use is made here of the DICOM standard. DICOM stands for "Digital Imaging and Communications in Medicine" and is a standard, which generally governs the structure of medical images, their aggregation options, their dispatch and their handling.

A software module E3.2 can be responsible for administering index structures, with such an index being allocated to existing images, thereby allowing a search for such images. The index structures are also structured according to DICOM (information: patient/study/series) and they are stored in a database.

A software module E3.3 can be responsible for the creation of medical reports, it being possible for such reports to be structured according to the rules of the DICOM structure report.

A software module E3.4 can be responsible for ensuring that the applications A1, A2, A3 can be administered in certain work steps across the hospital as a whole.

A software module E3.5 can administer protocols for hardware, such protocols describing sequences which are followed by medical modalities (image recording systems) during image recording. The software module E3.5 then contains a database of the protocols for different modalities.

Further tasks can be distributed on the third level, for example the monitoring of resources in applications, in other words the deployment of a set of rules in an application that relates to a resource, so that for example a certain storage unit usage can be assigned to an application. Standard medical protocols can also be implemented on the third level. "Patient data captured" etc. can for example be recorded in respect of application A3.

Software modules, which can be used by a plurality of applications, are disposed in particular on the fourth level. The hierarchical structure means that the software module or the associated program code only has to be provided once in the software platform as a whole and be stored once on a storage unit. Such a software platform design thus saves storage space, in particular compared with applications, in which sub-routines of applications are called up and integrated in a respective program.

The software module E4B has a special role, being able to be called up from both the third level and the fourth level. It is thus in an intermediate position between the fourth and fifth levels, so that the software modules of the actual fourth level are numbered "E4A" here, while the "B" in "E4B" indicates that it is to a certain degree of a lower order than the software modules shown as "E4A".

A software module E4A.1 can be responsible for example for storing DICOM files in the file system. The files are only stored in the directory for a short while, e.g. for the period of an examination performed with the aid of an application. However the software module E4A.1 can also have an archive for the permanent storage of medical images. Communication between the third level and the software module E4A takes place by way of a protocol P3, e.g. the DICOM protocol or even by way of "OS File Access". An interface S3 for this is provided in the third level and in the software module E4A.1, the general interface S of the third level also comprising S3.

The software module E4A.2 is a database system, it being possible to use an oracle system for example. It has an interface S4 to match the general interface S of the third level, which also comprises S4, so that it is possible to communicate by way of a protocol P4, a database protocol.

The software module E4A.3 is responsible for the administration of the portal PT and contains rules, which influence the appearance of the portal for various situations and auxiliary conditions. The software module E4A.3 has an interface S5 to match the general interface S and can communicate according to the protocol P5, e.g. HTTP.

The software modules E4A.1 to E4A.3 can be stored on storage units, which are different from the storage units on which higher-level software modules are stored and they can also run on different data processing facilities from these.

The software module E4B can take on the task of communication, namely transmitting messages either within the hospital or between hospitals. The software module E4B thus has a bus function. Its ability to be called up from both the third and fourth levels is because communication from the third level may be necessary. FIG. 1 shows interface S3 as the interface, so that it is possible to communicate by way of a protocol P3, which is also used with one of the other software modules E4A.1. However in contrast to the diagram a specific protocol can also be used for the software module E4B, (in this instance P6). One protocol that is suitable for the bus function of the software module E4B is DICOM or even SQL/XML Query.

Use of the interfaces S1 to S5 makes it possible, as described above, to move software modules from different levels to different computer units, in other words store them on storage units and run them on data processing facilities.

FIG. 2 shows four concepts of how this is possible:

According to the first concept the first to third groups of software modules E1 to E3 are disposed on a client computer system. The term "client" relates to the arrangement in the hospital, in particular in a department where the applications A1, A2 and A3 are required.

In the second concept only the software modules of the first and second groups are disposed on the client, with those of the third group being disposed on a server. The server can be disposed in the hospital but the invention allows such a server in particular to be moved outside the hospital. Hospital personnel are then not responsible for installing, maintaining and updating the software modules E3.1 to E3.5.

In the third concept only level E1 is disposed on the client, while the second and third groups are disposed on a server. It should be noted that in this instance level E1 and level E2 are separated. This is possible due to the application of the principles from U.S. Pat. No. 6,275,871 B1, even if the applications A1, A2 and A3 respectively require software from both levels.

In the fourth concept program code packages from all three groups are disposed on different computer units according to the three levels, namely the program code packages of the first group for the first level E1 on a client, where the application is required, the program code packages of the second group on a first server and the program code packages of the third group on a third server. There is therefore a separation between level E1 and level E2 and the software packages of the third level, E3.1 to E3.5. It is possible here for the client to be disposed in a hospital department, the first server at a central location in the hospital and the second server outside the hospital. The software modules are then optimally distributed and can be installed, maintained and updated respectively where personnel are optimally deployed for this purpose.

FIG. 2 only shows a specific distribution for the first to third groups. It is assumed that the software modules E4A.1 to E4A.3 and E4B are essentially disposed on a server. In concepts two to four this server can be identical to the server assigned respectively to the third group.

In all four concepts it is possible to distribute the program code packages of the third group (software modules E3.1 to E3.5) or those of the fourth group (software modules of the fourth level, E4A.1, E4A.2, E4B) to different servers (storage unit and data processing facility); it being thus possible for the separation to different servers to take place within the third level and also within the fourth level.

Moving software modules to central points in the hospital and in particular also to locations outside the hospital means that the hospital no longer has to deal with activities relating to the running of software, which also allows a cost saving in particular to be achieved.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LIST OF REFERENCE CHARACTERS

A1, A2, A3 Applications
E1, E2; E3.1, E3.2, Software modules of different levels E
E3.3, E3.4 and E3.5;
E4A, E4A.1, E4B
PT Portal
UA1, UA2, UA3 Sub-applications
S; S1, S2, S3, S4, S5 Software interfaces
P1, P2, P3, P4, P5, P6 Protocols

What is claimed is:

1. A program code including a number of groups, each having at least one program code package group, embedded on non-transitory computer readable storage units, each program code package, when run on the first data processing facility, causing steps to be performed in a sequence, the groups being ordered hierarchically such that in a step performed on the basis of a program code package of a level of the hierarchy, the performance of steps is brought about by running a program code package of the level of the hierarchy following the level, comprising:

program code packages from two groups, which follow one another in the hierarchical order, including program code package parts which bring about the performance of respective steps such that in a step performed on the basis of a program code package of a first group, at least one data item is sent when calling up a program code package of a second group, which is received in a step performed on the basis of said program code package of the second group, the program code package parts being designed so that the at least one data item can be sent by way of a data line from the first data processing facility at a first location, where said step on the basis of said program code package of the first group is performed, to a second data processing facility at a second location, where said step on the basis of a program code package of the second group is performed.

2. The program code as claimed in claim 1, wherein in all group pairs of groups, which follow one another in the hierarchical order, the program code packages from both groups have program code package parts which allow the transmission of data by way of a data line between two data processing facilities at different locations.

3. The program code as claimed in claim 1, wherein different groups including at least one program code package are stored on different storage units with a respectively assigned data processing facility.

4. The program code as claimed in claim 3, wherein all the groups including at least one program code package are stored respectively on a different storage unit with a respectively different assigned data processing facility.

5. The program code as claimed in claim 1, wherein in at least one group different program code packages from said group are stored on different storage units with a respectively assigned data processing facility.

6. The program code as claimed in claim 3, wherein at least one storage unit with a respectively assigned data processing facility is disposed in a hospital and at least one storage unit with an assigned data processing facility is disposed outside a hospital.

7. The program code as claimed in claim 1, wherein all the groups including at least one program code package are stored on a storage unit with an assigned data processing facility, which is located in a hospital.

8. The program code as claimed in claim 1, wherein a relatively highest group in the hierarchical order with at least one program code package comprises a program code package, which when running, brings about the performance of at least one step as a function of a user input.

9. The program code as claimed in claim 8, wherein a relatively second highest group in the hierarchical order with at least one program code package comprises a program code package which, on performance of a step brought about by the running of a program code package from the relatively highest group in the hierarchical order as a function of a user input, also brings about the performance of at least one step as a function of this user input.

10. The program code as claimed in claim 1, wherein a group with at least one program code package that is of a relatively lower order in the hierarchical order than another group comprises a program code package, which, when at least two different program code packages from the other group are respectively run, is respectively prompted in a step in turn to bring about the performance of a step when running.

11. A storage medium comprising the program code as claimed in claim 1.

12. The storage medium as claimed in claim 11, further comprising at least two storage units, associated respectively with a specific computer unit with a data processing facility.

13. A method for processing data based on operating instructions by way of a user interface disposed in a hospital, comprising:

causing via an operating instruction, in an chain of data processing facilities including at least two elements, a step performed by a first data processing facility at a first location in the chain respectively to bring about performance of at least one step by a subsequent data processing facility at a second location in the chain, wherein the steps to be performed are ordered hierarchically such that the performance of the at least one step at the subsequent data processing facility is of a level of the hierarchy following a level of the hierarchy of the step performed by the first data processing facility, wherein at least one data item is sent by way of a data line from said first data processing facility to said subsequent data processing facility for calling up a program code package of a second group of program code packages, wherein the data processing facility from the chain which executes a step brought about by the operating instruction, is disposed outside the hospital.

14. The method as claimed in claim 13, wherein the data processing facility disposed outside the hospital is an at least third data processing facility in the chain.

15. The program code as claimed in claim 2, wherein different groups including at least one program code package are stored on different storage units with a respectively assigned data processing facility.

16. The program code as claimed in claim 15, wherein all the groups including at least one program code package are stored respectively on a different storage unit with a respectively different assigned data processing facility.

17. The program code as claimed in claim 4, wherein at least one storage unit with a respectively assigned data processing facility is disposed in a hospital and at least one storage unit with an assigned data processing facility is disposed outside a hospital.

18. The program code as claimed in claim 2, wherein all the groups including at least one program code package are stored on a storage unit with an assigned data processing facility, which is located in a hospital.

19. The program code as claimed in claim 5, wherein at least one storage unit with a respectively assigned data processing facility is disposed in a hospital and at least one storage unit with an assigned data processing facility is disposed outside a hospital.

20. A non-transitory computer readable medium including program segments for, when executed on a computer device, causing the computer device to implement the method of claim 13.

21. A non-transitory computer readable medium including program code including a number of groups, each having at least one program code package group, stored on storage units, each program code package, when run on a data processing facility, causing steps to be performed in a sequence, the groups being ordered hierarchically such that in a step performed on the basis of a program code package of a level of the hierarchy, the performance of steps being brought about by running a program code package of the level of the hierarchy following the level, wherein program code packages from two groups, which follow one another in the hierarchical order, include program code package parts which bring about the performance of respective steps such that in a step performed on the basis of a program code package of a first group, at least one data item is sent, which is received in a step performed on the basis of a program code package of a second group, the program code package parts being designed so that the at least one data item can be sent by way of a data line for calling up a program code package of the second group from a first data processing facility at a first location, where said step on the basis of said program code package of the first group is performed, to a data processing facility at a second location, where said step on the basis of a program code package of the second group is performed.

\* \* \* \* \*